United States Patent [19]

Branch

[11] Patent Number: 5,520,691
[45] Date of Patent: May 28, 1996

[54] METHOD AND APPARATUS FOR RE-APPROXIMATING TISSUE

[76] Inventor: Thomas P. Branch, 655 Greystone Park, Atlanta, Ga. 30324

[21] Appl. No.: 354,582

[22] Filed: Dec. 13, 1994

Related U.S. Application Data

[63] Continuation of Ser. No. 609,886, Nov. 6, 1990, Pat. No. 5,372,146.

[51] Int. Cl.⁶ .................................................. A61B 19/00
[52] U.S. Cl. ........................ 606/72; 606/216; 606/232; 24/16 PB; 24/30.5 P
[58] Field of Search ................................... 606/151, 216, 606/232, 223, 138, 128, 72; 24/16 PB, 30.5 P, 17 AP

[56] References Cited

U.S. PATENT DOCUMENTS

| | | |
|---|---|---|
| 27,357 | 4/1967 | Merser . |
| 3,072,986 | 1/1963 | Lefnaer .................. 24/16 PB |
| 3,290,080 | 12/1964 | Dawson . |
| 3,973,299 | 8/1976 | Keefe . |
| 4,069,825 | 1/1978 | Akiyama ................ 606/138 |
| 4,245,374 | 1/1981 | Suzuki . |
| 4,669,473 | 6/1987 | Richards et al. ............ 606/232 |
| 4,708,132 | 11/1987 | Silvestrini . |
| 4,711,002 | 12/1987 | Kreeger ................... 24/30.5 P |
| 4,741,330 | 5/1988 | Hayhurst . |
| 4,784,126 | 11/1988 | Hourahane . |
| 4,872,451 | 10/1989 | Moore et al. . |
| 4,889,110 | 12/1989 | Galline et al. . |

OTHER PUBLICATIONS

Mitek Surgicial Products, Inc., single–page flyer, entitled "MITEK GII Anchor–High Strength Fixation", Flyer No. 90021-3/91.

Zimmer, Inc. sals brochure, entitled "STATAK Soft Tissue Attachment Device", Flyer No. 97–2344–01 1988.

Acufex Microsurgical, Inc., sales brochure, Introducing TAG™: the System for secure tissue re–attchment, Flyer No. 398310.

*Primary Examiner*—Gary Jackson
*Attorney, Agent, or Firm*—Jones & Askew

[57] ABSTRACT

Methods and apparatuses are described for attaching tendons, ligaments, or other tissue to bone, which includes the use of adjustable head members positioned along filament members. Also disclosed are methods and apparatuses for mending breaks in tissue such as skin or meniscal layers tissue such as skin or meniscal layers skin by use of similar elements.

15 Claims, 4 Drawing Sheets

METHOD AND APPARATUS FOR RE-APPROXIMATING TISSUE

This is a continuation of application Ser. No. 609,886, filed Nov. 6, 1990, now U.S. Pat. No. 5,372,146.

TECHNICAL FIELD

This invention relates in general to surgically-related methods and apparatuses, and more particularly relates to methods and apparatuses for re-approximating, or re-attaching, a tendon or ligament to a bone, when the same have become separated due to injury or other circumstances. The invention also relates to methods and apparatuses for reattaching tissue such as skin edges or meniscal layers after such tissue has been torn, cut, or otherwise severed. Due to the relatively simple embodiments of the present invention, the invention also may be used in conjunction with arthroscopic procedures, minimally invasive surgical procedures utilizing tiny incisions and a fiber optic camera.

BACKGROUND OF THE INVENTION

In surgical practice, a genuine need often exists for a reliable, simple, and effective means for re-attaching tendons, ligaments, or other tissue which have become separated from the bone of a human or animal. Such separation may be due to injury, genetic defects, or may be the result of various surgical procedures.

It is preferable to re-attach such a tendon or ligament to the bone such that it may eventually heal and attach itself to the bone. In such a configuration, it may be understood that the attachment of the ligament or tendon to the bone must be sufficient to withstand loads seen during rehabilitation, which may include loads necessitated by physical therapy.

If the tendon or ligament cannot be attached to the bone such that grafting would occur, the attachment must be sufficient to withstand loads encountered not only during rehabilitation, but for the rest of the-patient's life.

It may be understood that particular needs are presented by such re-attachment requirements, such as a need to expediently perform the re-attachment procedure in order that the patient undergoes minimal trauma, as well as a need to provide a minimally-sized incision, in order to reduce the risk of infection and to minimize scarring.

A number of prior art methods and devices have been developed in order to address the above-discussed needs. However, the prior art known to the applicant does not adequately satisfy these needs.

It is known to utilize pliable sutures in order to attach tissue to bone, or tissue to tissue, by passing the suture through or around such elements, and subsequently hand tying the sutures in place. However, such methods are disadvantageous as it is difficult to determine the proper mount of tension to be applied to the sutures such that the sutures maintain adequate holding strength but do not break. Other disadvantages arise in that the space allowed to perform such tying techniques may be generally limited.

It is also generally known to staple ligaments or tendons to a bone, although such a method has significant drawbacks. If the staple is positioned too loosely, the ligament or tendon may become detached by slipping underneath the staple. If the staple is positioned too tightly on the bone, the ligament or tendon may be severed or "guillotined" by the staple, or disadvantageous tissue necrosis or death may occur.

U.S. Pat. No. 4,708,132 to Silvestrini, entitled "Fixation Device for a Ligament or Tendon Prosthesis", issued Nov. 24, 1987, discloses a device for affixing a pretensioned ligament or tendon prosthesis to a bone of a patient. It may be seen that a relatively complex anchor device is utilized, which requires the drilling of holes completely through various bones of the patient, necessarily requiring extensive surgical procedures.

U.S. Pat. No. 4,784,126 to Hourahane, entitled "Surgical Device", issued Nov. 15, 1988, discloses another method for surgery of which requires drilling of hole completely through a bone of a patient, such that on elongated clamp may be passed through the rear opening of the hole, in order to clasp a ligament and draw it through the front opening of the hole.

U.S. Pat. No. 5,482,451 to Moore, entitled "Glenohumeral Ligament Repair", issued Oct. 10, 1989, discloses a ligament repair kit and procedure for installing a. cannulated bone screw and ligament washer to retain a ligament on a bone. Further disclosed is a screw which is screwed to tighten a spiked ligament washer against the displaced ligaments to firmly hold them in place against the bone.

U.S. Pat. No. 4,889,110 to Galline et at., entitled "Attaching Device and Tools for Positioning Same, Especially for Attaching Trochanter Major to the Femur", issued Dec. 26, 1989, discloses an attaching device including an anchoring plate having four bores which receive two crimping tubes and two crimping rings for holding a multi-ply cable. The device is adapted to be used for attaching the trochanter major to the femur in the case of a trochanteric osteotomy.

Although at least some of the above patents do generally disclose attachment of a detached ligament to a bone, they include disadvantages in that they utilize complex attachment devices and procedures. Furthermore, the disclosed techniques require in some cases severe surgical incisions in order to access patient bone areas for drilling, which may disadvantageously cause patient trauma, unacceptable scarring, or infection.

Therefore, there is a need in the art to provide a reliable, simple, and effective means for re-attaching a tendon or ligament to a bone, in which minimal patient trauma is encountered, and minimum infection or scarring results.

SUMMARY OF THE INVENTION

The present invention addresses the above-discussed deficiencies in the prior an by providing a reliable, simple, and effective means for attaching a tendon or ligament to a bone, with a minimum of patient trauma, exposure to infection, and scarring.

Generally described, a method according to the present invention comprises the steps of attaching a first end of a flexible, elongate, filament member to a bone, the filament member including a first protruding portion, and including a first reduced portion intermediate the first end and the first protruding portion, and defining a second end opposing the first end; threading the second end of the filament member through an internal hole defined by a head member, the head member also defining engagement means extending into the hole, the engagement means configured to engage the first protruding portion to a greater extent than the tint reduced portion; urging the head member along the filament member toward the first end and away from the second end with a force sufficient to urge the engagement member across the protruding section of the filament member until the engagement member is positioned atop the reduced section and the tissue member is captured between the head member and the bone.

Therefore it is an object of the present invention to provide a method and apparatus for re-attaching tendons, ligaments, or other tissue to bone.

It is a further object of the present invention to provide a method and apparatus for repairing a skin break.

It is a further object of the present invention to provide a method and apparatus for re-attaching tendons, ligaments, or other tissue to bone while providing minimal exposure to infection.

It is a further object of the present invention to provide a method and apparatus for re-attaching a tendon, ligament, or other tissue to a bone which do not require complete drilling through the bone.

It is a further object of the present invention to provide a method and apparatus for re-attaching a tendon, ligament, or other tissue to a bone which are especially suitable for use in conjunction with arthroscopic procedures.

It is a further object of the present invention to provide a method and apparatus for re-attaching severed tissue which are especially suitable for use in conjunction with arthroscopic procedures.

It is a further object of the present invention to provide a method and apparatus for re-attaching a tendon, ligament, or other tissue to a bone which require a minimal amount of surgical incision.

It is a further object of the present invention to provide a means for re-attaching a tendon, ligament, or other tissue to a bone, which allows the tissue to eventually graft to the bone.

Other objects, feature, and advantages of the present invention will become apparent from reading the following specification when taken in conjunction with the accompanying drawings.

DETAILED DESCRIPTION OF THE PREFERRED EMBODIMENT

Figure 1:
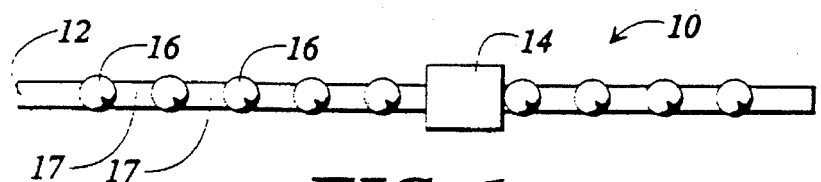
FIG. 1 is a side view of a fastening system including a filament member and a head member mounted thereon.

Referring now in more detail to the drawings, in which like numerals indicate like parts throughout the several views, FIG. 1 illustrates a fastening system 10, including an elongate flexible filament member 12, and a head member 14 slidably mounted thereupon. The filament member 12 includes a plurality of uniformly spaced-apart protruding sections including protrusions 16. The filament member 12 also includes a plurality of uniformly spaced-apart reduced sections 17 intermediate the protrusions 16. The engagement member 18 interferes with the protrusions 16 of the filament of a greater degree than with the reduced sections 17 of the filament.

Figure 2:
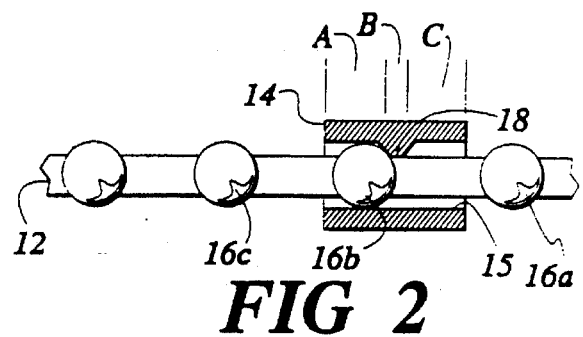
FIG. 2 is a more detailed view of the interaction of the head member and the filament member illustrated in FIG. 1.

Referring also to FIG. 2, the head member 14 defines an inner bore 15, which includes two bore portions "A" and "C" having substantially uniform and similar transverse cross sections, and an intermediate bore portion "B" having a transverse cross-section less in area than that of bore portions "A" and "C", due to the existence of engagement member 18, which is intended to contact the protrusions 16. The protrusions 16 pass with relative ease through portions "A" and "C" of the bore 15, but the engagement member 18 contacts the protrusions within bore portion "B". A protrusion 16 will not pass by the engagement member until after a force has been applied by the protrusion against the engagement member sufficient to deflect or deform either the engagement member or the protrusion, or a combination thereof, such that the protrusion can pass by the engagement member.

As may be understood, as the filament member 12 is moved left to right as shown in the drawings relative to head 14, protrusion 16a will be the first to contact and then pass by engagement member 18. This may also be referred to as passing the engagement member across the protrusion. Subsequently, another protrusion 16b will encounter the engagement member 18. During such a process, it may be understood that intermittent levels of force will be required to draw the filament member 12 past the engagement member 18; just as the protrusions 16 are provided in a generally uniformly spaced-apart relationship along the filament member 12, so will various intermittent force "peaks" be required in order to pass the filament member 12 through the head member 14.

Therefore it may be understood that filament members such as 12 may pass through head members such as 14, with the above-described interference tending to cause the engagement member 18 of the head to tend to remain between the protrusions and atop the reduced portions 17 such as shown in FIG. 2, unless a force is provided to overcome the above described interference. A head-sleeve relationship as shown in FIG. 2 is such that it would be seen if a leftward force was applied to the head 14 and a rightward force was applied to the filament 12, but said forces were insufficient to overcome the engagement between the engagement member 18 and the protrusion 16b.

Figure 3:
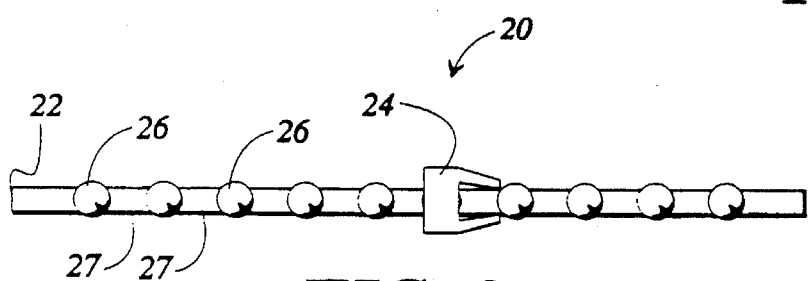
FIG. 3 is a side view of a second fastening system including a filament and a head member mounted thereon.

Referring now to FIG. 3, a fastening system 20 is shown, including a head member 24 interacting with a filament member 22 having spaced-apart protrusions 26, and spaced apart reduced portions 27.

The filament has a substantially circular cross-section, although the areas of such cross-section may vary depending on whether the cross-section is taken through the protrusions or reduced portions. The head member includes a main body defining a substantially circular hole (not shown) through which the filament passes, and also includes a pair of flange members 35, although three or more flange members may be used. The flange members 35 extend from the main body of the head member (extending left to right as shown in the drawings) and terminate to define a shoulder 37 intended to contact the protrusions 36. The free ends of the flange members-may be seen to provide "engagement means" for engaging the protrusions 36 of the filament.

It may be understood that the free ends of flange members 35 are deflected radially outwardly relative to the longitudinal axis of the filament member 32 as the filament member is drawn left to right relative to the head 34 and the flange members pass across the protrusions. It may also be understood that intermittent force "peaks" as discussed above are encountered, as the flange members 35 interfere with the protrusions 36 to a greater extent than with the reduced portions 32 of the filament member. It finally may be understood that if the filament member 32 is caused to move right to left relative to the head 34, the shoulders 37 of the protrusions 36 will tend to prevent such movement, and preferably much higher force "peaks" would be encountered in moving the filament right to left relative to the head compared to the force peaks encountered in moving the filament left to right. In fact, it may not be possible to create such movement without damaging either the filament or the head.

Figure 4:
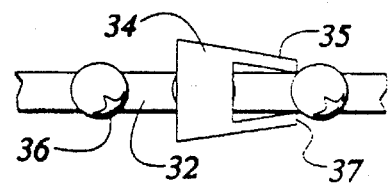
FIG. 4 is a more derailed view of the interaction of the head member and the filament member illustrated in FIG. 3.
Figure 5:
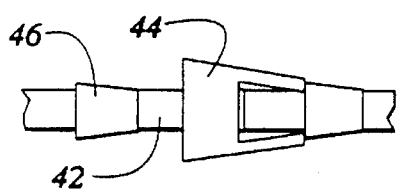
FIGS. 5 and 6 are other detailed views similar to that of FIG. 4, illustrating other filament-head configurations.
Figure 6:
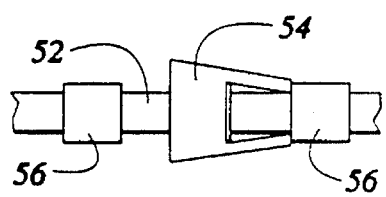

FIGS. 4–6 illustrate further filament-head configurations in which protrusions and reduced portions exist on the filaments.

Figure 7:
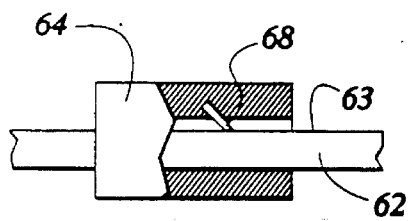
FIG. 7 is detailed view of a filament member having a substantially constant transverse cross-section, used in connection with a head member having a engaging blade.
Figure 8:
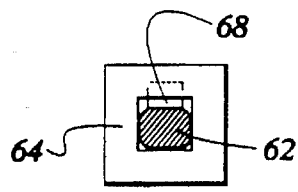
FIG. 8 is a cross-sectional end view of that shown in FIG. 7.

FIGS. 7 and 8 illustrate a filament-head configuration in which a filament member 62 has a relatively smooth surface 63 which is engaged by an engagement member or blade 68 mounted within an internal hole defined by a head member 64. As the filament member 62 is moved left to right relative to the head member 64, the edge of the blade 68 which contacts the surface 63 of the filament member 62 slides across the surface 63 of the filament member 62. However, should the filament member 62 be urged right to left relative to the head member 64, the relatively sharp nature of the blade 68 restricts such movement as the edge tends to engage or "bite into" the filament member. Therefore, it may be seen that the configuration illustrated in FIG. 7 is such that the filament member-may move left to right relatively easily, but is discouraged from moving right to left relative to the head member 64.

It may be noted that the surface 63 of the filament member 62 may be smooth, or also may have a serrated surface to encourage engagement of the blade 68 into the filament member. Such a serrated configuration is similar.

Other fastening systems including filament members used in non-medical applications, are disclosed in U.S. Pat. Nos. 3,290,080, Re. 27,357, 3,973,299, and 4,245,374, all of which are incorporated by reference.

In the configurations shown in FIGS. 1–6, the transverse cross-section of the filaments at any position along their lengths is substantially circular. Therefore, a collar member may rotate about its associated filament member, but such rotation alone will not cause it to travel longitudinally along the filament member such as by a screw action. In the configuration shown in FIGS. 7 and 8, the rectangular transverse cross-section of the filament 62 and the similarly-shaped inner slot defined by the collar member 64 does not allow the collar to twist relative to the filament. This non-twist feature may be advantageous in the collar (or a washer affixed thereto) may be positioned against a tendon or ligament as discussed below, and rotation of the collar may be reduced or prevented.

The above-discussed filaments and heads may be made of inert materials such as polyethylene, nylon, or other suitable polymeric materials, if the connection is desired to be permanent. If the connection is desired to be temporary, degradable materials such as polyglactin (provided under the trade name VICRYL, or polydioxanone (PDS) may be used.

As shown above, many different fastening systems including filaments and heads are disclosed in reference to FIGS. 1–8. These fastening systems may be used interchangeably in many of the following applications to the surgical field.

Figure 9:
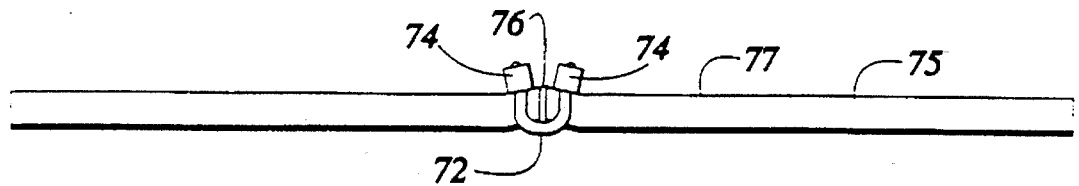
FIG. 9 is a side view of a fastening system applied to a skin, meniscal layer, or other tissue break, according to the present invention.

Referring now to FIG. 9, a filament member 72 is used in combination with a pair of head members 74, in order to provide a suture to mend a break in human or animal tissue 75 such as that at 76. The tissue member may, for example, be a meniscal layer or a skin layer.

The filament member 72 is threaded through two adjoining tissue portions on opposing sides of the tissue break 76, much as a typical thread would be attached to a needle and passed through such tissue members in order to mend them by a typical stitch.

After the filament member 72 has been passed through the tissue and each of its ends extend above one side of the tissue (preferably the outer surface of skin tissue), the head members may then be placed on each end of the filament members and then urged toward the center of the filament, until the head members are adjusted to contact the tissue surface layer at 77, and until a desired tautness of the filament member 72 between the head members is obtained. At this time, any excess filament length extending above the heads may be trimmed as desired. Other similar sutures could be provided depending on the size and length of the tissue break.

It should be understood that the two portions of the filament which actually lie within the tissue layer may be understood to be "inside" the tissue. If the tissue is skin, the head members would preferably be on the "outside" of the skin (the side exposed to the elements), biasing on the "outside" surface of the skin.

It should also be understood that another installation method may be used to arrive at the configuration shown in FIG. 9. One head member 74 may be placed on one end of the filament member 72 prior to insertion of the filament into the tissue, with the opposing end of the filament then being passed through both of the tissue portions. At that time, only one head member would be required to be placed on the other end of the filament member.

Furthermore, also contemplated is the use of a fixed "head" (not shown), attached to one end of the filament to replace one of the above-described heads illustrated in FIG. 9. Such a configuration would require only one adjustable head to be placed on one end of the filament, after the filament has been passed through the tissue. Such a fixed head could be as that known as a ZIMMER STATAK device available from Zimmer, Inc., P.O. Box 708, Warsaw, Ind., 46590-0708, illustrated in catalog no. 2344-10, disclosed in U.S. Pat. No. 4,632,100 and incorporated herein by reference.

Note that alternate configurations could be used to attached the tissue at its break described above. For example meniscal or skin layers could be overlapped, with a fixed T-shaped head (discussed in further detail below) attached to one end of the filament and forced through the overlapped tissue, with a head member subsequently placed on the filament end opposite the T-shaped head and pushed toward the T-shaped head to squeeze the overlapped skin therebetween. In such a configuration, the filament portion intermediate the two heads would preferably be in tension and substantially straight. Such a configuration would be especially qualified for use with arthroscopic techniques.

Figure 10:
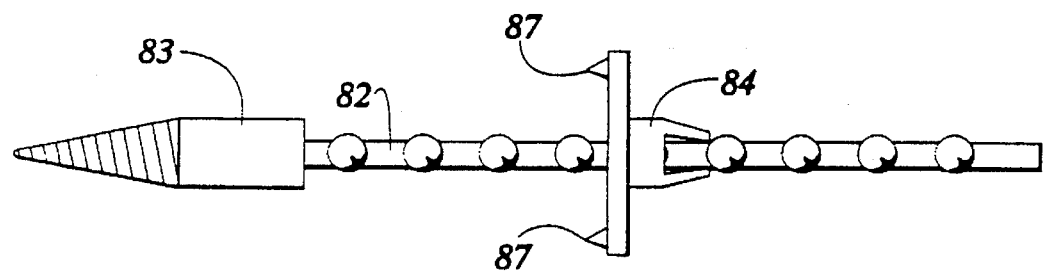
FIG. 10 is a side view of a fastening system for use in attaching a tendon to a bone according to the present invention.
Figure 11:
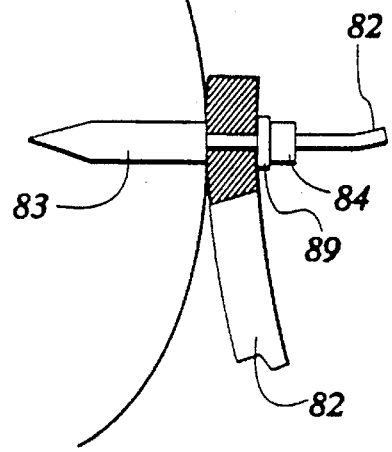
FIG. 11 is a side view of a fastening system such as that shown in FIG. 10 used to attach a tendon to a bone according to the present invention.

Referring now to FIGS. 10 and 11, a filament member 82 is used in combination with an anchor member 83 and a head member 84 in order to maintain a tissue member 86 such as a tendon or ligament in surface contact with a bone 88. The anchor member 83 is attached to one end of the filament member. Installation of the anchor member into the bone allows the filament member 82 to be attached to the bone 88 approximate the area at which the tissue is desired to be attached to the bone 83.

After installation of the anchor member, the filament member 82 is threaded through tissue member 86 (piercing it if necessary) is subsequently threaded through a washer 89, and finally is threaded through a head member 84 such as that described as 24 in the fastening system shown in FIG. 3. At that point, the filament 82 is preferably maintained in a tensile state by pulling on it while the head 84 is pushed along the filament 82 (such that the engagement member or members of the head 84 pass by the protrusions on the filament 82) until the tissue is snug against the surface 90 of the bone 88, the washer 89 is snug against the tendon 86, and the head 84 is snug against the washer 89. Such snugness is provided by the virtue of engagement of the engagement member of the head with one of the protrusions. Excess filament may then be trimmed.

It may be understood that a separate washer 89 may be used as described above, or another type of head may be used which incorporates an integral flange which serves the same purpose of the above-described washer.

As shown in FIG. 10, the washer may include a plurality of spikes 87, which may be used to engage the tissue to prevent slippage. The size and configuration of the spikes may vary depending on the nature of the particular application.

Figure 14:
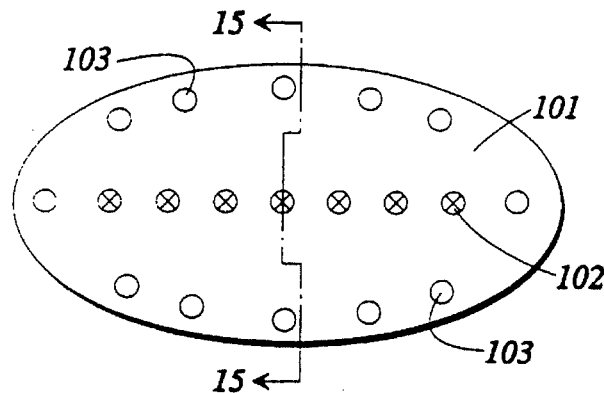
FIG. 14 is a lower plan view of a spiked head according to the present invention used to accept a plurality of filament members.
Figure 15:
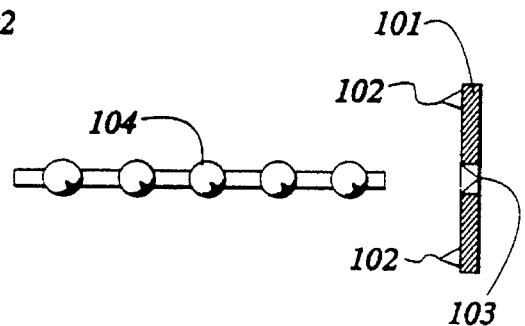
FIG. 15 is a side cross-sectional view of the head of FIG. 14, illustrating only two spikes.

As shown in FIGS. 14 and 15, a multi-filament head 101 may be used which includes a plurality of one-way holes 103 for accepting a plurality of filaments such as 104 which have been affixed in a localized bone region. Such an application may be advantageous in situations where a large or broad tissue member is to be affixed to a bone. Such multi-filament configurations may also be used if it is not desired to pierce the tissue member; two filament members could be used to attach a head atop a tissue member, with the filament members being positioned on either side of the; tissue without piercing it.

Figure 12:
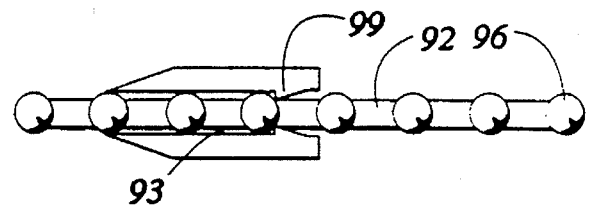
FIG. 12 is a detailed view of an anchoring member used to anchor a filament member to a bone according to the present invention.
Figure 13:
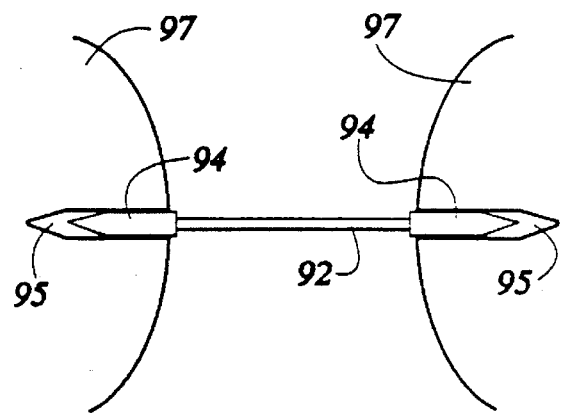
FIG. 13 is a side plan view of a fastening system used to link two bone members together according to the present invention.

Referring now to FIG. 12, a filament 92 is used in combination with a pair of externally-threaded anchor members 94. Referring also to FIG. 13, the anchor members 94 are screwed into respective cavities 95 drilled into bone members 97. The anchor members 94 each have a central longitudinal bore 93 which passes entirely through each anchor member 94. Within the bore 93 extends at least one engagement member 99 which interacts with protrusions 96 defined by filament 92 as discussed above. Note that instead of the engagement member 99 being positioned within a head such as that described above, the engagement member is positioned within the internal bore of 93 the anchor member, which accepts the filament 92.

When both of the anchor members 94 are positioned within holes 95 in the respective bone members 97, each end of the filament member 92 is placed within a respective anchor member 94. At that time, the filament member 92 is pushed into the anchor members 94 until a desired length of the filament extending between the bones is obtained. As the bores 93 extend completely through the anchor members 94, there is some space for the ends of the filament 92 to pass through the anchor member and into the end of the cavity 97 drilled into the bone. As the filament member is preferably somewhat flexible, it may even be possible that although one end of the filament member may "bottom out" in the cavity, it could still be able to be pushed further into the cavity, as it may fold over itself or bend.

An alternative configuration to that shown in FIG. 13 includes a pair of anchor members, but with only a first anchor member including an internal engagement means as described above. The second anchor member is affixed to one end of the filament, with no adjusting capability. In such a configuration, the filament will only be adjusted within the anchor member including the engagement means.

Referring now again to FIGS. 1–6, various filaments and heads are shown. It may understood that these heads are what may be termed as "one-way" or "two-way" heads, and some of the filaments may be understood as "one-way" or "two-way" filaments.

Referring to FIGS. 1 and 2, filament 12 may be referred to a "two-way" filament, as its protrusions 16 are configured such that a head passing in one direction along the filament will encounter substantially the same resistance than the head passing in a second, opposite direction. This is of course assuming that the restricted portion of the head bore encountering the protrusions is the same, such as the case with head 14, which may be referred to as a "two-way" head. It may be understood that such a configuration is such that the engagement member and the protrusion member interact such that the maximum force required to urge the engagement member by a protrusion in one direction is approximately the same as the maximum force required to urge the engagement member by the protrusion in a second, opposing, direction.

Referring now to FIGS. 3 and 4, filament 32 may be considered a "two-way" filament. However, the head 34 positioned thereon may be considered a "one-way" filament, as such a head moving left to right relative to the filament will encounter more resistance than the same head moving right to left. Such a configuration is at times preferable when one wishes to move such a head in one direction, but does not wish the head to move in the opposite direction. It may be understood that such a configuration is such that the engagement member and the protrusion member interact such that the maximum force required to urge the engagement member by a protrusion in one direction is less than the maximum force required to urge the engagement member by the protrusion in a second, opposing, direction.

Using the above criteria, FIG. 5 illustrates a "one-way" head is shown positioned on a "one-way" filament 42.

In reference to FIG. 6, a "one-way" head is shown positioned on a "two-way" filament.

In reference to FIGS. 7 and 8, the filament 62 may be considered a "two-way" filament, while the head positioned thereon may be considered a "one-way" head.

Figure 16:
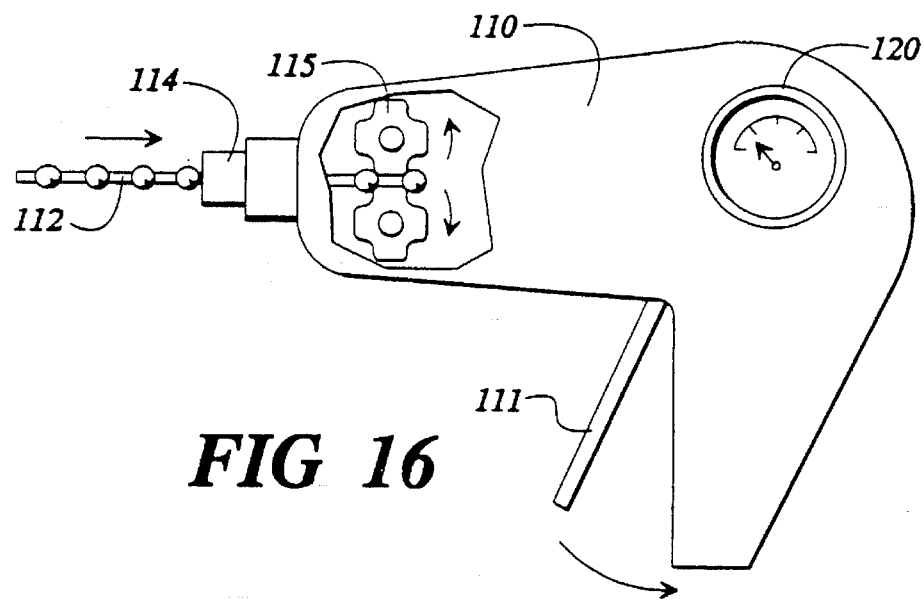
FIG. 16 is a side view of an installation tool according to the present invention used to install fastening systems.

Referring now to FIG. 16, an installation tool 110 is illustrated for use is urging a typical head 114 along a typical filament 112, such that the head moves in a right to left direction relative to the filament 112. The installation tool 110 includes a trigger 111, and a force gauge 120, which is read to determine the mount of force used to draw the filament 112 through the collar 114.

It should be understood that such force is needed to overcome the above-discussed requirements of deflecting any engagement members within the collar 114, but an opposing tensile force on the filament 112 may also be present if the filament has been attached to a bone or has been .threaded through tissue as described above.

An illustration of the use of the installation tool 110 is now described as such a tool might be used in order to affix the tendon 86 to the bone 88 as shown in FIG. 11. The filament 82 would be inserted into a hole (not shown) in the "nose" of the installation tool 110, and an internal mechanism including a pair of grasping sprockets 115 would cooperate to grasp that end of the filament.

The grasping sprockets are mounted for driven rotation about substantially parallel spaced-apart axes, such that radially extended teeth of each sprocket cooperate to bias against protrusions of a filament in order to draw the ligament into the tool. The tool may be configured to work with any of the filaments and heads shown in FIGS. 1–6. For use in connection with the filament and head shown in FIGS. 7 and 8, the means for grasping the filament would need to be modified.

When the filament 82 is in proper position within the tool, the trigger 111 of the tool 110 is pulled, causing the internal mechanism to pull on the filament, such that it is caused to drown into the tool. When the collar finally contacts the nose of the tool 110 (such as the collar 114 is contacting the tool in FIG. 16), the movement of the collar relative to the tool 110 will be prevented, thus causing the filament to be dram through the collar 114.

At this time, the operator will monitor the force gauge 120. As discussed above, eventually the nut 84 is pushed into contact with the washer 89, and the washer 89 is pushed into contact with the tendon 86, which is likewise urged against the surface 90 of the bone 88. As such elements are drawn close together such as shown in FIG. 11, the operator will monitor the force dial 120 with care. Depending on his or her experience with the particular ligament or tendon being attached to the bone, the operator will recognize when a desired force is read on the dial, and will then terminate operation of the tool. The tool will the be withdrawn, and the filament may be trimmed as discussed above. The gun may optionally have an internal mechanism which recognizes a pre-set force exerted on the filament, and will automatically disengage at that point. The gun may also optionally have a filament cutting mechanism.

Figure 17:
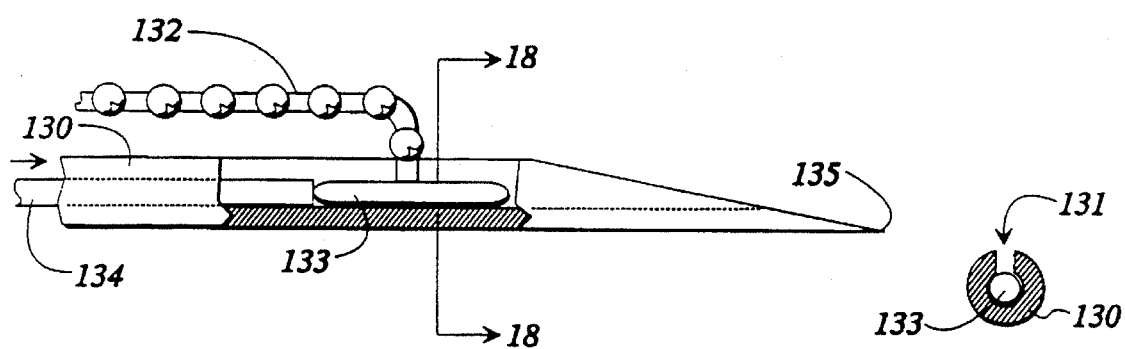
FIG. 17 is a side, partially cut away view of an installation needle according to the present invention used to install fastening systems.
Figure 18:
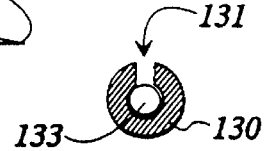
FIG. 18 is an end cross-sectional view of the needle shown in FIG. 17.

Another contemplated use of filaments in the surgical field is shown in FIGS. 17 and 18. A slotted needle 130 includes an elongate slot 131 running along its length. A filament 132 includes a T-shaped head 133 attached to one of its ends. This head may loaded into the slot of the needle 130 and placed in end-to-end contact with a urging pin 134 which is configured to slide within the slot 131 of the needle. After the tip 135 of the needle 130 has been passed through one or more layers of tissue (not shown), an urging mechanism (not shown) is activated such that the urging pin 134 pushes the head 133 of the filament (left to-fight in reference to FIG. 17) such that the head exits the needle, straightens out, and is positioned on one side of the tissue resisting retraction therethrough, while the opposing end of the filament is on the opposite side of the tissue. If the filament has been passed through two layers of tissue (such as shown in FIG. 9), a cooperating head such as 24 shown in FIG. 3 may be placed on the filament and pushed along the filament as discussed above such that the two tissue members may be attached via the filament-heads combination.

Such a configuration as shown in FIGS. 17 and 18 is especially suitable for use during arthroscopic procedures, by the use of specially designed insertion tools (not shown). It may be understood that the relatively simple fastening configuration provided by the invention would not require unduly complex arthroscopic tools.

Figure 19:
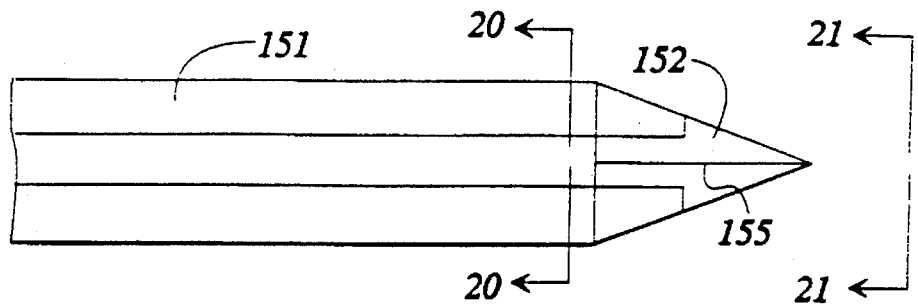
FIG. 19 is a partial top planned view of a second installation needle according the present invention used to install fastening systems.
Figure 20:
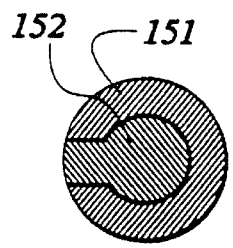
FIG. 20 is a cross-sectional view along line 20—20 of FIG. 19.
Figure 21:
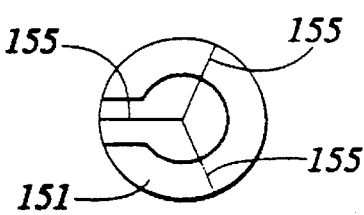
FIG. 21 is an in plan view of the needle illustrated in FIG. 19.

Referring now generally to FIGS. 19–22, a second installation needle system 150 is disclosed, which includes a sleeve 151, and an internal styler 152, which slidably fits within a slot defined by the sleeve 151. The sleeve and the stylet combine as shown in FIG. 19 to form a generally cylindrical, pointed member, in which the point is generally defined by three faces meeting at edges 155 (see also FIG. 21). The system 150 may used to attach a tendon 160 to a bone including a cortical bone wall 162, and internal cancellous bone 163. The cancellous bone is softer than the conical bone.

Figure 22:
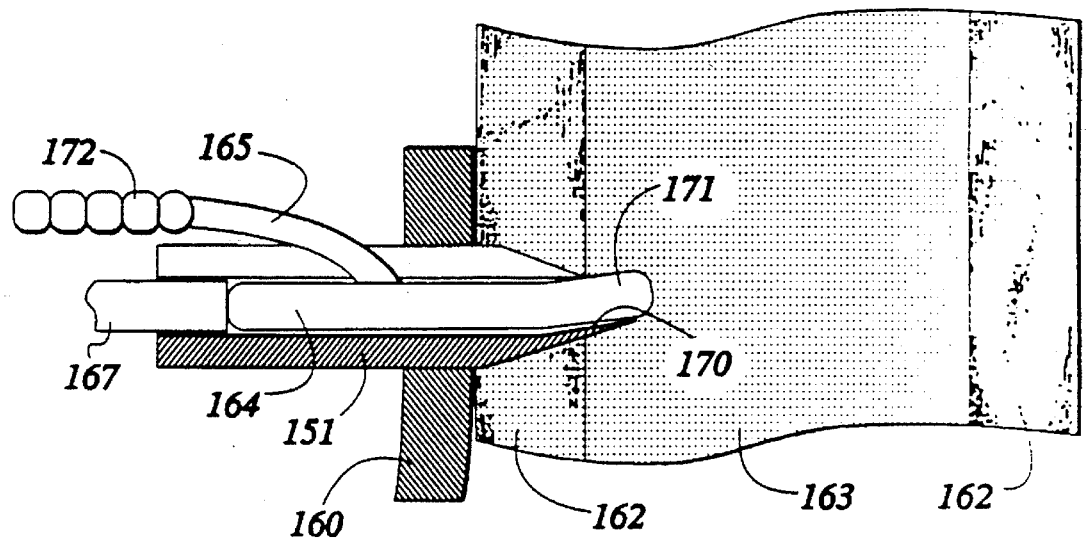
FIG. 22 is a partial cross-sectional view of a portion of the needle illustrated in FIG. 19, illustrating the use of the needle and installing a T-shaped member into a bone.

Referring now to FIG. 22, in order to fasten the tendon or other tissue 160 to the bone, the point of the needle system 150 is passed through the tendon 160, and thereafter driven or rotated into the bone, such that the tip of the needle system 150 passes through the cortical wall 162. At that point, the styler is withdrawn from the sleeve, and the head 164 of a T-shaped member 165 is placed within the slot. Thereafter, a driving member 167 is activated in order that the head is driven through the sleeve, past the cortical bone, and into the cancellous bone region. It may be seen that the curved portion 170 defined by the sleeve urges the leading tip 171 of the head of the T-shaped member in an upward direction away from the installation axis of the head.

After the head 164 is installed within the cancellous bone region, the sleeve 151 is withdrawn. It may be understood that as the T-shaped member has been urged in the above-referenced upward direction, a subsequent pull on the filament 172 will cause the "T" to lie snug and flat against the inside surface of the cancellous bone 162, and it will be discouraged from being subsequently withdrawn through the hole left by the needle system 150. Alternatively, the cancellous bone could be of sufficient stiffness to capture the "T" on its own, such that the "T" may not be positioned against the inside surface of the cortical bone. After the "T"

is in place, a head member (not shown) may be placed upon the filament portion 172 of the T-shaped member 165, as described above. Note that the close proximity of the projections on the filament member 172 still provide for intermediate reduced portions, and such a configuration is contemplated under the present invention.

Therefore, it may be seen that methods and apparatuses for attaching tendons, ligaments, or other tissue to bones is provided which do not require drastic drilling or other bone access preparations, and may be suitable for arthroscopic applications. Unlike some prior art methods, there is no need to drill completely through the bone. Unlike other prior methods, simple devices and methods are provided which include minimal parts and complexity.

Therefore, it may be seen that the present invention provides methods and apparatuses for providing reliable, simple, and effective means for reattaching tendons, ligaments, or other tissue which have become separated from the bone of a human or animal. The invention also provides a means for providing a suture in order to mend a break in a skin layer, a meniscal layer, or other tissue. The methods and apparatuses allow a surgeon or other qualified personnel to expediently perform repair procedures, using arthroscopic procedures if possible, in order that the patient undergoes minimal trauma as well as experiences minimal infection or scarring due to a reduced need for incision.

It should be understood that the foregoing relates only to preferred embodiments of the present invention, and that numerous modifications or alterations may be made therein without departing the spirit and scope of the invention as set forth in the appended claims.

What is claimed is:

1. A device for attaching an elongate, flexible filament member to a bone, said bone defining a pre-drilled bone hole therein, comprising:
    an elongate flexible filament and
    an anchor member defining an external surface configured to engage said pre-drilled bone hole and secure said anchor member relative to said hole, said anchor member also defining an internal bore to be substantially aligned with said hole and configured to accept a length of said filament member, said anchor member also defining an internal engagement means configured to engage said length of said flexible filament member within said anchor to discourage removal of said filament from said anchor when it is in place in said bone.

2. The device as claimed in claim 1, wherein said filament member includes a plurality of protruding portions separated by reduced portions, and wherein said anchor member bore is a central longitudinal bore, and said engagement means is configured to engage said protruding portions to a greater extent than said reduced portions, to allow said filament to be secured at a variety of positions relative to said anchor member.

3. The device as claimed in claim 2, further comprising a head member configured for attachment to said filament member to facilitate securement of tissue relative thereto.

4. The device as claimed in claim 2, further comprising a second anchor member configured for attachment relative to said filament member to facilitate securement of tissue relative thereto.

5. The device as claimed in claim 1, further comprising a head member configured for attachment to said filament member to facilitate securement of tissue relative thereto.

6. The device as claimed in claim 1, further comprising a second anchor member configured for attachment relative to said filament member to facilitate securement of a second bone member relative thereto.

7. A device for attaching a first bone to a second bone, said first bone defining a pre-drilled bone hole therein, said device comprising:
    an elongate, flexible filament member,
    a first anchor member defining an external surface configured to engage said pre-drilled hole and secure said anchor member relative to said first bone, said anchor member also defining an internal bore to be substantially aligned with said pre-drilled hole and configured to accept a first end of said filament member, said anchor member also defining an engagement means configured to engage said flexible filament member within said first anchor have to discourage removal of said filament from said first anchor member when in place in said bone; and
    a second anchor member for attaching said second end of said filament member to said second bone.

8. The device as claimed in claim 7, wherein said second bone also defines a pre-drilled second hole therein, and wherein said second anchor member defines an external surface configured to engage said pre-drilled second hole and secure said anchor member relative to said second bone, said second anchor member also defining an internal second bore substantially aligned with said pre-drilled hole and configured to accept a second length of said filament member, said second anchor member also defining an engagement means configured to engage said second length of said flexible filament member within said second anchor have to discourage removal of said filament from said second anchor member when in place in said bone.

9. The device as claimed in claim 8, wherein said filament member includes a plurality of protruding portions separated by reduced portions, and wherein said first anchor member bore is a central longitudinal bore, and said engagement means of said first anchor member is configured to engage said protruding portions to a greater extent than said reduced portions, to allow said filament to be secured at a variety of positions relative to said first anchor member.

10. The device as claimed in claim 7, wherein said filament member includes a plurality of protruding portions separated by reduced portions, and wherein said first anchor member bore is a central longitudinal bore, and said engagement means of said first anchor member is configured to engage said protruding portions to a greater extent than said reduced portions, to allow said filament to be secured at a variety of positions relative to said first anchor member.

11. The anchor member as claimed in claim 10, wherein said external surface of said first anchor member is threaded to facilitate threaded engagement with said pre-drilled hole in said bone.

12. The anchor member as claimed in claim 7, wherein said external surface of said first anchor member is threaded to facilitate threaded engagement with said pre-drilled hole in said bone.

13. A device for attaching tissue to bone, comprising:
    a filament member defining opposing first and second ends and including a first protruding portion, a first reduced portion having a cross-sectional area less than that of said protruding portion, said reduced portion located intermediate said first end and said first protruding portion, said filament also including a threadable portion capable of being threaded through said tissue, said threadable portion being intermediate said first end and said reduced portion;

an anchor member located at said first end for attaching said first end of said filament member to said bone; and a head member movable relative to said filament and defining an internal hole extending therethrough for accepting said filament and also defining engagement means extending into said hole, said engagement means configured to engage said first portion to a greater extent than said first reduced portion, said engagement member engaging said protrusion and restricting movement of said head member toward said second end of said filament member and said head member likewise restricting movement of said tissue away from said bone.

14. The device as claimed in claim 13, wherein said anchor member defines a central longitudinal bore to allow said filament to be secured therein at a variety of positions relative to said anchor member.

15. The device as claimed in claim 13, wherein said filament member includes a plurality of protruding portions separated by reduced portions, and wherein said anchor member defines a central longitudinal bore including engagement means therein configured to engage said protruding portions to a greater extent than said reduced portions, to allow said filament to be secured at a variety of positions relative to said anchor member.

* * * * *